United States Patent
Kondo et al.

(10) Patent No.: US 7,183,441 B2
(45) Date of Patent: Feb. 27, 2007

(54) METHOD FOR PRODUCING VICINAL DITHIOL

(75) Inventors: Mitsuteru Kondo, Tokyo (JP); Motoharu Takeuchi, Tokyo (JP); Masahiro Johno, Tokyo (JP); Kenji Ishii, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 178 days.

(21) Appl. No.: 11/058,354

(22) Filed: Feb. 16, 2005

(65) Prior Publication Data

US 2005/0187413 A1    Aug. 25, 2005

(30) Foreign Application Priority Data

Feb. 17, 2004  (JP) .............................. 2004-040619

(51) Int. Cl.
*C07C 319/02*  (2006.01)
(52) U.S. Cl. .......................................... 568/63; 568/66
(58) Field of Classification Search ..................... None
See application file for complete search history.

(56) References Cited

U.S. PATENT DOCUMENTS 3,369,040 A * 2/1968 De Acetis ..................... 560/87
5,087,759 A * 2/1992 Vallee et al. .................. 568/66
2003/0195270 A1   10/2003 Ishii et al.

FOREIGN PATENT DOCUMENTS

JP          2004-107278        4/2004

OTHER PUBLICATIONS

"Some Reactions of Ethylene Sulfide, and a New Method of Preparation of Vicinal Dithiols", J. Chem Soc. (1948), 1894-95.*
Abstract for the article entitled "Preparation of 1,2-dithiols from Episulfides", Tetrahedron Letters (1973), 16, 1401-04.*
European Search Report, dated Jun. 21, 2005, for Application No. 05101082.5-1211.

* cited by examiner

*Primary Examiner*—Marc S. Zimmer
(74) *Attorney, Agent, or Firm*—Antonelli, Terry, Stout and Kraus, LLP.

(57) ABSTRACT

A vicinal dithiol is produced by the reaction of an episulfide compound having at least one thiirane ring in its molecule and a thiocarboxylic S-acid.

7 Claims, No Drawings

METHOD FOR PRODUCING VICINAL DITHIOL

BACKGROUND OF THE INVENTION

1. Field of the Invention

The present invention relates to a method for producing a vicinal dithiol which is useful for the production of optical materials such as plastic lenses, prisms, fiber optics, information recording media, filters and adhesives for optical devices.

2. Description of the Prior Art

Cured materials produced by the polymerization of an episulfide compound added with a sulfur-containing compound such as thiol compounds are widely used at present in the applications for spectacle plastic lenses because of their good balance between the refractive index and Abbe's number. The vicinal dithiol, above all, has a high sulfur content and is extremely suitable for such applications because of the ability of increasing the refractive index of cured materials and the ability of increasing the crosslinking density of resultant polymers.

In many of the proposed methods of producing the vicinal dithiol, a vicinal diol or a vicinal dihalide is reacted with thiourea. However, the proposed reactions involve side reactions such as polymerization, rearrangement, etc. and the vicinal dithiol is produced in low yields. In other proposed methods, a compound having a thiirane ring is reacted with hydrogen sulfide or an alkali metal hydrogen sulfide. However, these proposed methods also involve undesirable polymerization, etc. and give the vicinal dithiol only in low yields. For example, the reaction of ethylene sulfide and hydrogen sulfide at room temperature provides ethanedithiol in 49% yield (E. M. J. Meade, et al., J. Chem. Soc., 1894 (1948)). The reaction of cyclohexene sulfide and potassium hydrogen sulfide provides cyclohexanedithiol in 38% yield (C. C. J. Culvenor, et al., J. Chem. Soc., 282 (1949)).

SUMMARY OF THE INVENTION

An object of the present invention is to develop a method for producing a vicinal dithiol in high yields.

As a result of extensive research, the inventors have found that the vicinal dithiol is produced in high yields by the reaction of an episulfide compound having at least one thiirane ring in its molecule and a thiocarboxylic S-acid such as thioacetic S-acid. The present invention has been accomplished on the basis of this finding.

Thus, the invention provides a method for producing a vicinal dithiol comprising a step of reacting an episulfide compound having at least one thiirane ring in its molecule and a thiocarboxylic S-acid.

DETAILED DESCRIPTION OF THE INVENTION

The starting episulfide compound usable in the invention is not structurally limited as long as it has at least one thiirane ring in its molecule. In addition to the thiirane ring, the starting episulfide compound may have another functional group. The number of the thiirane ring is also not specifically limited.

In view of the crosslinking ability of resultant vicinal dithiol and the refractive index of cured materials which are to be produced by the addition of the vicinal dithiol, the episulfide compound represented by the following formula 1 is preferred as the starting raw material:

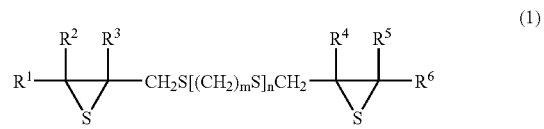

wherein $R^1$ to $R^6$ are each independently hydrogen or $C_1$–$C_{10}$ hydrocarbon group, m is an integer from 0 to 6, and n is an integer from 0 to 4.

Examples of the episulfide compounds include ethylene sulfide, propylene sulfide, cyclohexene sulfide, styrene sulfide, thioglycidol, thioglycidyl acetate, thioglycidyl propionate, thioglycidyl benzoate, 1,1-bis(epithioethyl)methane, 1-(epithioethyl)-1-(β-epithiopropyl)methane, 1,1-bis(β-epithiopropyl)methane, 1-(epithioethyl)-1-(β-epithiopropyl)ethane, 1,2-bis(β-epithiopropyl)ethane, 1-(epithioethyl)-3-(β-epithiopropyl)butane, 1,3-bis(β-epithiopropyl)propane, 1-(epithioethyl)-4-(β-epithiopropyl)pentane, 1,4-bis(β-epithiopropyl)butane, 1-(epithioethyl)-5-(β-epithiopropyl)hexane, 1-(epithioethyl)-2-(γ-epithiobutylthio)ethane, 1-(epithioethyl)-2-[2-(γ-epithiobutylthio)ethylthio]ethane, tetrakis(β-epithiopropyl)methane, 1,1,1-tris(β-epithiopropyl)propane, 1,3-bis(β-epithiopropyl)-1-(β-epithiopropyl)-2-thiapropane, 1,5-bis(β-epithiopropyl)-2,4-bis(β-epithiopropyl)-3-thiapentane, 1,3- or 1,4-bis(epithioethyl)cyclohexane, 1,3- or 1,4-bis(β-epithiopropyl)cyclohexane, bis[4-(epithioethyl)cyclohexyl]methane, bis[4-(β-epithiopropyl)cyclohexyl]methane, 2,2-bis[4-(epithioethyl)cyclohexyl]propane, 2,2-bis[4-(β-epithiopropyl)cyclohexyl]propane, bis[4-(β-epithiopropyl)cyclohexyl]sulfide, bis[4-(epithioethyl)cyclohexyl]sulfide, 2,5-bis(epithioethyl)-1,4-dithiane, 2,5-bis(β-epithiopropyl)-1,4-dithiane, 4-epithioethyl-1,2-cyclohexene sulfide, 4-epoxy-1,2-cyclohexene sulfide, methyl thioglycidyl ether, ethyl thioglycidyl ether, propyl thioglycidyl ether, butyl thioglycidyl ether, bis(β-epithiopropyl)ether, bis(β-epithiopropyloxy)methane, 1,2-bis(β-epithiopropyloxy)ethane, 1,3-bis(β-epithiopropyloxy)propane, 1,2-bis(β-epithiopropyloxy)propane, 1-(β-epithiopropyloxy)-2-(β-epithiopropyloxymethyl)propane, 1,4-bis(β-epithiopropyloxy)butane, 1,3-bis(β-epithiopropyloxy)butane, 1-(β-epithiopropyloxy)-3-(β-epithiopropyloxymethyl)butane, 1,5-bis(β-epithiopropyloxy)pentane, 1-(β-epithiopropyloxy)-4-(β-epithiopropyloxymethyl)pentane, 1,6-bis(β-epithiopropyloxy)hexane, 1-(β-epithiopropyloxy)-5-(β-epithiopropyloxymethyl)hexane, 1-(β-epithiopropyloxy)-2-[(2-β-epithiopropyloxyethyl)oxy]ethane, 1-(β-epithiopropyloxy)-2-[[2-(2-β-epithiopropyloxyethyl)oxyethyl]oxy]ethane, bis(5,6-epithio-3-oxahexyl)selenide, bis(5,6-epithio-3-oxahexyl)telluride, tetrakis(β-epithiopropyloxymethyl)methane, 1,1,1-tris(β-epithiopropyloxymethyl)propane, 1,5-bis(β-epithiopropyloxy)-2-(β-epithiopropyloxymethyl)-3-thiapentane, 1,5-bis(β-epithiopropyloxy)-2,4-bis(β-epithiopropyloxymethyl)-3-thiapentane, 1-(β-epithiopropyloxy)-2,2-bis(β-epithiopropyloxymethyl)-4-thiahexane, 1,5,6-tris(β-epithiopropyloxy)-4-(β-epithiopropyloxyniethyl)-3-thiahexane, 1,8-bis(β-epithiopropyloxy)-4-(β-epithiopropyloxymethyl)-3,6-dithiaoctane, 1,8-bis(β-epithiopropyloxy)-4,5-bis(β-epithiopropyloxymethyl)-3,6-dithiaoctane, 1,8-bis(β-epithiopropyloxy)-4,4-bis(β- epithiopropyloxymethyl)-3,6-dithiaoctane, 1,8-bis(β-epithiopropyloxy)-2,4,5-tris(β-epithiopropyloxymethyl)-3,6-dithiaoctane, 1,8-bis(β-epithiopropyloxy)-2,5-bis(β-epithiopropyloxymethyl)-3,6-dithiaoctane, 1,9-bis(β-epithiopropyloxy)-5-(β-epithiopropyloxymethyl)-5-[(2-β-epithiopropyloxyethyl)oxymethyl]-3,7-dithianonane, 1,10-bis(β-epithiopropyloxy)-5,6-bis[(2-β-epithiopropyloxyethyl)oxy]-3,6,9-trithiadecane, 1,11-bis(β-epithiopropyloxy)-4,8-bis(β-epithiopropyloxymethyl)-3,6,9-trithiaundecane, 1,11-bis(β-epithiopropyloxy)-5,7-bis(β-epithiopropyloxymethyl)-3,6,9-trithiaundecane, 1,11-bis(β-epithiopropyloxy)-5,7-[(2-β-epithiopropyloxyethyl)oxymethyl]-3,6,9-trithiaundecane, 1,11-bis(β-epithiopropyloxy)-4,7-bis(β-epithiopropyloxymethyl)-3,6,9-trithiaundecane, 1,3- or 1,4-bis(β-epithiopropyloxy)cyclohexane, 1,3- or 1,4-bis(β-epithiopropyloxymethyl)cyclohexane, bis[4-(β-epithiopropyloxy)cyclohexyl]methane, 2,2-bis[4-(β-epithiopropyloxy)cyclohexl]propane, bis[4-(β-epithiopropyloxy)cyclohexyl]sulfide, 2,5-bis(β-epithiopropyloxymethyl)-1,4-dithiane, 2,5-bis(β-epithiopropyloxyethyloxymethyl)-1,4-dithiane, 1,3- or 1,4-bis(β-epithiopropyloxy)benzene, 1,3- or 1,4-bis(β-epithiopropyloxymethyl)benzene, bis[4-(β-epithiopropyl)phenyl]methane, 2,2-bis[4-(β-epithiopropylthio)phenyl]propane, bis[4-(β-epithiopropylthio)phenyl]sulfide, bis[4-(β-epithiopropylthio)phenyl]sulfone, 4,4'-bis(β-epithiopropylthio)biphenyl, bis(β-epithiopropyl)sulfide, bis(β-epithiopropyl)disulfide, bis(β-epithiopropyl)trisulfide, bis(β-epithiopropylthio)methane, 1,2-bis(β-epithiopropylthio)ethane, 1,3-bis(β-epithiopropylthio)propane, 1,2-bis(β-epithiopropylthio)propane, 1-(β-epithiopropylthio)-2-(β-epithiopropylthiomethyl)propane, 1,4-bis(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl)pentane, 1,6-bis(β-epithiopropylthio)hexane, 1-(β-epithiopropylthio)-5-(β-epithiopropylthiomethyl)hexane, 1-(β-epithiopropylthio)-2-[(2-β-epithiopropylthioethyl)thio]ethane, 1-(β-epithiopropylthio)-2-[[2-(2-β-epithiopropylthioethyl)thioethyl]thio]ethane, tetrakis(β-epithiopropylthiomethyl)methane, 1,1,1-tris(β-epithiopropylthiomethyl)propane, 1,5-bis(β-epithiopropylthio)-2-(β-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(β-epithiopropylthio)-4-(β-epithiopropylthiomethyl)-3-thiahexane, 1,8-bis(β-epithiopropylthio)-4-(β-epithiopropylthiomethyl)-3,6-dithiaoctane, 1,8-bis(β-epithiopropylthio)-4,5-bis(β-epithiopropylthiomethyl)-3,6-dithiaoctane, 1,8-bis(β-epithiopropylthio)-4,4-bis(β-epithiopropylthiomethyl)-3,6-dithiaoctane, 1,8-bis(β-epithiopropylthio)-2,4,5-tris(β-epithiopropylthiomethyl)-3,6-dithiaoctane, 1,8-bis(β-epithiopropylthio)-2,5-bis(β-epithiopropylthiomethyl)-3,6-dithiaoctane, 1,9-bis(β-epithiopropylthio)-5-(β-epithiopropylthiomethyl)-5-[(2-β-epithiopropylthioethyl)thiomethyl]-3,7-dithianonane, 1,10-bis(β-epithiopropylthio)-5,6-bis[(2-β-epithiopropylthioethyl)thio]-3,6,9-trithiadecane, 1,11-bis(β-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6,9-trithiaundecane, 1,11-bis(β-epithiopropylthio)-5,7-[(2-β-epithiopropylthioethyl)thiomethyl]-3,6,9-trithiaundecane, 1,11-bis(β-epithiopropylthio)-4,7-bis(β-epithiopropylthiomethyl)-3,6,9-trithiaundecane, 1,3- or 1,4-bis(β-epithiopropylthio)benzene, 1,3- or 1,4-bis(β-epithiopropylthiomethyl)benzene, bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl]sulfone, 4,4'-bis(β-epithiopropylthio)biphenyl, bis(β-epithiopropyl)selenide, bis(β-epithiopropyl)diselenide, bis(β-epithiopropyl)triselenide, bis(β-epithiopropylseleno)methane, bis(β-epithiopropyl)telluride, bis(β-epithiopropyl)ditelluride, bis(β-epithiopropyl)tritelluride, bis(β-epithiopropyltelluro)methane, 1,2-bis(β-epithiopropyltelluro)ethane, vinylphenyl thioglycidyl ether, vinylbenzyl thioglycidyl ether, thioglycidyl methacrylate, thioglycidyl acrylate, allyl thioglycidyl ether, and compounds derived from the preceding episulfide compounds by substituting methyl group for at least one hydrogen of the epithio group, with bis(β-epithiopropyl)sulfide and bis(β-epithiopropyl)disulfide being preferred.

The episulfide compound having at least one thiirane ring in its molecule usable in the invention is not specifically limited to examples recited above, and the above compounds may be used alone or in combination of two or more.

The method of the invention comprises a first step of reacting the episulfide compound and the thiocarboxylic S-acid represented by the following formula 2:

(2)

wherein $R^7$ is a hydrocarbon group having 1 to 7 carbon atoms, in the presence of a base to produce a thiocarboxylic S-ester; a second step of hydrolyzing the thiocarboxylic S-ester in the presence of a base to produce a mercaptide; and a third step of converting the mercaptide into the vicinal dithiol in the presence of an acid. Example of the production scheme is shown below.

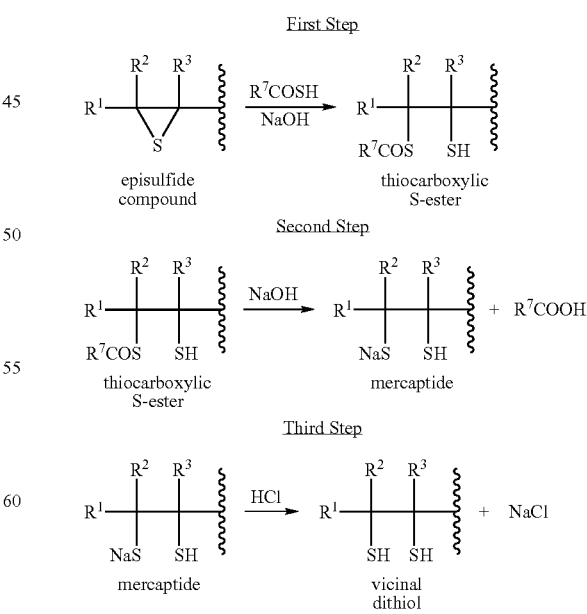

wherein $R^1$, $R^2$, $R^3$ and $R^7$ are as defined above.

In the first step, the thiirane ring of the episulfide compound is opened in the presence of the base to produce the thiocarboxylic S-ester. Examples of the thiocarboxylic S-acid of the formula 2 include thioacetic S-acid, thiopropionic S-acid, thiobutyric S-acid, thiobenzoic S-acid, etc., with thioacetic S-acid being particularly preferred. The thiocarboxylic S-acid is used in an amount so as to regulate the ratio of the total molar number of the mercaptocarbonyl groups in the thiocarboxylic S-acid to the total molar number of thiirane rings in the episulfide compound within the range of preferably 0.1 to 10, more preferably 0.5 to 5, and still more preferably 0.9 to 2.

The base is selected from the group consisting of ammonia, amines, phosphines, metal alcoholates, metal hydrides, metal hydroxides, metal carbonates and metal sulfides. The amount of the base to be used is preferably 0.0001 to 1 mol, more preferably 0.001 to 0.3 mol, and still more preferably 0.001 to 0.1 mol per one mole of the episulfide compound.

Examples of the base are shown below.

(1) Ammonia (2) Amines:

primary amines such as ethylamine, n-propylamine, sec-propylamine, n-butylamine, sec-butylamine, isobutylamine, tert-butylamine, pentylamine, hexylamine, heptylamine, octylamine, decylamine, laurylamine, myristylamine, 1,2-dimethylhexylamine, 3-pentylamine, 2-ethylhexylamine, allylamine, aminoethanol, 1-aminopropanol, 2-aminopropanol, aminobutanol, aminopentanol, aminohexanol, 3-ethoxypropylamine, 3-propoxypropylamine, 3-isopropoxypropylamine, 3-butoxypropylamine, 3-isobutoxypropylamine, 3-(2-ethylhexyloxy)propylamine, aminocyclopentane, aminocyclohexane, aminonorbornene, aminomethylcyclohexane, aminobenzene, benzylamine, phenetylamine, α-phenylethylamine, naphthylamine and furfurylamine; primary polyamines such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, dimethylaminopropylamine, diethylaminopropylamine, bis(3-aminopropyl)ether, 1,2-bis(3-aminopropoxy)ethane, 1,3-bis(3-aminopropoxy)-2,2'-dimethylpropane, aminoethylethanolamine, 1,2-, 1,3- or 1,4-diaminocyclohexane, 1,3- or 1,4-bis(aminomethyl) cyclohexane, 1,3- or 1,4-bis(aminoethyl)cyclohexane, 1,3- or 1,4-bis(aminopropyl)cyclohexane, hydrogenated 4,4'-diaminodiphenylmethane, 2- or 4-aminopiperidine, 2- or 4-aminomethylpiperidine, 2- or 4-aminoethylpiperidine, N-(aminoethyl)piperidine, N-(aminopropyl)piperidine, N-(aminoethyl)morpholine, N-(aminopropyl)morpholine, isophoronediamine, menthanediamine, 1,4-bis(aminopropyl)piperadine, o-, m- or p-phenylenediamine, 2,4- or 2,6-tolylenediamine, 2,4-toluenediamine, m-aminobenzylamine, 4-chloro-o-phenylenediamine, tetrachloro-o-xylylenediamine, 4-methoxy-6-methyl-m-phenylenediamine, m- or p-xylylenediamine, 1,5- or 2,6-naphthalenediamine, benzidine, 4,4'-bis(o-toluidine), dianisidine, 4,4'-diaminodiphenylmethane, 2,2-(4,4'-diaminodiphenyl)propane, 4,4'-diaminodiphenyl ether, 4,4'-thiodianiline, 4,4'-diaminodiphenyl sulfone, 4,4'-diaminoditolyl sulfone, methylenebis(o-chloroaniline), 3,9-bis(3-aminopropyl)-2,4,8,10-tetraoxaspiro[5.5]undecane, diethylenetriamine, iminobis(propylamine), methyliminobis(propylamine), bis(hexamethylene)triamine, triethylenetetramine, tetraethylenepentamine, pentaethylenehexamine, N-(aminoethyl)piperadine, N-(aminopropyl) piperadine, 1,4-bis(aminoethyl)piperadine, 1,4-bis(aminopropyl)piperadine, 2,6-diaminopyridine and bis(3,4-diaminophenyl)sulfone;

secondary amines such as diethylamine, dipropylamine, di-n-butylamine, di-sec-butylamine, diisobutylamine, di-n-pentylamine, di-3-pentylamine, dihexylamine, dioctylamine, di(2-ethylhexyl)amine, methylhexylamine, diallylamine, pyrrolidine, piperidine, 2-, 3- or 4-picoline, 2,4-, 2,6- or 3,5-lupetidine, diphenylamine, N-methylaniline, N-ethylaniline, dibenzylamine, methylbenzylamine, dinaphthylamie, pyrrol, indoline, indole and morpholine;

secondary polyamines such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperadine, 2-methylpiperadine, 2,5- or 2,6-dimethylpiperadine, homopiperadine, 1,1-di(4-piperidyl)methane, 1,2-di(4-piperidy)ethane, 1,3-di(4-piperidyl)propane, 1,4-di(4-piperidyl)butane and tetramethylguanidine;

tertiary amines such as trimethylamine, triethylamine, tri-n-propylamine, triisopropylamine, tri(1,2-dimethylpropyl) amine, tri(3-methoxypropyl)amine, tri-n-butylamine, tri-isobutylamine, tri-sec-butylamine, tri-n-pentylamine, tri-3-pentylamine, tri-n-hexylamine, tri-n-octylamine, tri(2-ethylhexyl)amine, tridodecylamine, trilaurylamine, dicyclohexylethylamine, cyclohexyldiethylamine, tricyclohexylamine, N,N-dimethylhexylamine, N-methyldihexylamine, N,N-dimethylcyclohexylamine, N-methyldicyclohexylamine, N,N-diethylethanolamine, N,N-dimethylethanolamine, N-ethyldiethanolamine, triethanolamine, tribenzylamine, N,N-dimethylbenzylamine, diethylbenzylamine, triphenylamine, N,N-dimethylamino-p-cresol, N,N-dimethylaminomethylphenol, 2-(N,N-dimethylaminomethyl)phenol, N,N-dimethylaniline, N,N-diethylaniline, pyridine, quinoline, N-methylmorpholine, N-methylpiperidine and 2-(2-dimethylaminoethoxy)-4-methyl-1,3,2-dioxabornane;

tertiary polyamines such as tetramethylethylenediamine, pyrazine, N,N'-dimethylpiperadine, N,N'-bis(2-hydroxypropyl)piperadine, hexamethylenetetramine, N,N,N',N'-tetramethyl-1,3-butaneamine, 2-dimethylamino-2-hydroxypropane, diethyaminoethanol, N,N,N-tris(3-dimethylaminopropyl)amine, 2,4,6-tris(N,N,-dimethylaminomethyl)phenol and heptamethylisobiguanide;

imidazole compounds such as imidazole, N-methylimidazole, 2-methylimidazole, 4-methylimidazole, N-ethylimidazole, 2-ethylimidazole, 4-ethylimidazole, N-butylimidazole, 2-butylimidazole, N-undecylimidazole, 2-undecylimidazole, N-phenylimidazole, 2-phenylimidazole, N-benzylimidazole, 2-benzylimidazole, 1-benzyl-2-methylimidazole, N-(2'-cyanoethyl)-2-methylimidazole, N-(2'-cycanoethyl)-2-undecylimidazole, N-(2'-cyanoethyl)-2-phenylimidazole, 3,3-bis(2-ethyl-4-methylimidazolyl)methane, 2-mercaptoimidazole, 2-mercapto-N-methylimidazole, 2-mercaptobenzimidazole, 3-mercapto-4-methyl-1,2,4-triazole, 5-mercapto-1-methyl-tetrazole, 2,5-dimercapto-1,3,4-thiadiazole, addition products of alkylimidazoles and isocyanuric acid and condensation products of alkylimidazoles and formaldehyde; and amidines such as 1,8-diazabicyclo[5.4.0]undecene-7,1,5-diazabicyclo[4.3.0]nonene-5,6-dibutylamino-1,8-diazabicyclo[5.4.0]undecene-7.

(3) Phosphines:

trimethylphosphine, triethylphosphine, triisopropylphosphine, tri-n-butylphosphine, tri-n-hexylphosphine, tri-n-octylphosphine, tricyclohexylphosphine, triphenylphosphine, tribenzylphosphine, tris(2-methylphenyl) phosphine, tris(3-methylphenyl)phosphine, tris(4-methylphenyl)phosphine, tris(diethylamino)phosphine, tris(4-methylphenyl)phosphine, dimethylphenylphosphine, diethylphenylphosphine, dicyclohexylphenylphosphine, ethyldiphenylphosphine, diphenylcyclohexylphosphine and chlorodiphenylphosphine (4) Metal Alcoholates:

lithium methoxide, sodium methoxide, potassium methoxide, magnesium methoxide, calcium methoxide, sodium ethoxide, potassium ethoxide, sodium t-butoxide, and potassium t-butoxide.

(5) Metal Hydrides:

lithium hydride, sodium hydride, potassium hydride, magnesium hydride, calcium hydride, sodium borohydride and lithium aluminum hydride.

(6) Metal Hydroxides:

lithium hydroxide, sodium hydroxide, potassium hydroxide, magnesium hydroxide, calcium hydroxide, barium hydroxide and aluminum hydroxide.

(7) Metal Carbonates:

lithium carbonate, sodium carbonate, sodium hydrogencarbonate, potassium carbonate, potassium hydrogencarbonate, magnesium carbonate, calcium carbonate, barium carbonate, aluminum carbonate, cadmium carbonate, nickel carbonate, copper carbonate, strontium carbonate, cobalt carbonate and manganese carbonate.

(8) Metal Sulfides:

sodium sulfide, sodium hydrogensulfide, potassium sulfide, potassium hydrogensulfide, zinc sulfide, mercury sulfide and iron sulfide.

The base usable in the first step is not specifically limited to the examples recited above, and the above bases may be used alone or in combination of two or more. Among the exemplified bases, relatively preferred are metal hydroxides, with sodium hydroxide and potassium hydroxide being more preferred.

The solvent for use in the first step is preferably a polar organic solvent having a high dissolving power to thiocarboxylic S-acid and base, and alcohols are more preferably used. The amount of the solvent to be used is selected so that the ratio, (weight of episulfide compound)/(total weight of solvent and episulfide compound), is preferably 0.05 to 0.5, more preferably 0.1 to 0.4, and still more preferably 0.2 to 0.3.

Examples of the solvent include, but not limited thereto, methanol, ethanol, n-propanol, isopropanol, n-butanol, isobutanol, sec-butanol, tert-butanol, n-amyl alcohol, active amyl alcohol, isoamyl alcohol, sec-amyl alcohol, 3-pentanol, tert-amyl alcohol, fusel oil, n-hexanol, methylamyl alcohol, 2-ethylbutanol, n-heptanol, 2-heptanol, 3-heptanol, n-octanol, 2-octanol, 2-ethylhexanol, 3,5,5-trimethylhexanol, nonanol, n-decanol, undecanol, n-dodecanol, trimethylnonyl alcohol, tetradecanol, heptadecanol, ethylene glycol, diethylene glycol, triethylene glycol, tetraethylene glycol, polyethylene glycol, propylene glycol, dipropylene glycol, polypropylene glycol, hexylene glycol, octylene glycol, glycerol, trimethylolpropane, and 1,2,6-hexanetriol, with methanol and ethanol being preferred. The solvents may be used alone or in combination of two or more.

The reaction temperature of the first step is selected depending on the kinds of solvent, base, etc. to be used, and preferably 20 to 100° C., more preferably 30 to 80° C., and still more preferably 40 to 60° C.

The reaction of the first step is carried out, for example, by adding dropwise the episulfide compound directly or in a solution thereof into a uniform solution of the thiocarboxylic S-acid, base and solvent under stirring. It is preferred to complete the dropwise addition preferably within one minute to six hours, more preferably within 5 min to 3 h, and still more preferably 15 min to 2 h. After the dropwise addition, it is preferred to continue the stirring of the reaction liquid mixture preferably for 10 min to 24 h, more preferably for 30 min to 20 h, and still more preferably for 1 to 12 h to allow the reaction to further proceed. As described below, it is preferred to reduce the oxygen concentration of the reaction atmosphere to 5% by volume or less, for example, by introducing an inert gas such as nitrogen gas. After the reaction, the reaction product liquid of the first step is subjected to the next reaction of the second step generally without separation, purification, etc.

In the second step, the thiocarboxylic S-ester from the first step is hydrolyzed in the presence of the base to produce the mercaptide. The base for use in the second step is preferably selected from those described above with respect to the first step. The base for use in the second step is added in an amount so as to regulate the ratio of the total effective amount represented by the following formula:

$$\text{total effective amount} = V \times M \qquad (1)$$

wherein V is the valency of the base and M is the total molar number of the base used in the first step and the base to be added in the second step, to the total molar number of mercaptocarbonyl groups in the thiocarboxylic S-acid used in the first step within the range of preferably 0.1 to 10, more preferably 0.5 to 5, and still more preferably 0.9 to 3. The base for the second step and the base for the first step may be different types, but preferably the same type in view of production efficiency.

The reaction temperature of the second step largely influences the by-production of oligomers, etc. The by-production of oligomers, etc. can be prevented by carrying out the reaction at low temperatures, but the reaction time is prolonged. Therefore, it is not preferred for the production efficiency to unduly reduce the reaction temperature. Particularly, the reaction time of the second step greatly depends on the reaction temperature. To prevent the by-production of oligomers, etc. and to complete the reaction within a short period of time, the reaction temperature is preferably −20 to 40° C., more preferably −10 to 30° C., and still more preferably 0 to 20° C. It is also preferred for the second step to carry out the reaction in an atmosphere having an oxygen concentration of 5% by volume or less.

In the second step, the base is added dropwise to the reaction product liquid from the first step directly or in a solution (preferably 20% by weight to a saturated concentration, or a saturated concentration if the saturated concentration is lower than 20% by weight) preferably over one minute to six hours, more preferably 10 min to 3 h, and still more preferably 30 min to 2 h under stirring. After the dropwise addition, it is preferred to continue the stirring of the reaction liquid preferably for 10 min to 24 h, more preferably for 30 min to 20 h, and still more preferably for 1 to 12 h to allow the reaction to further proceed. The reaction product liquid of the second step is subjected to the next reaction of the third step generally without separation, purification, etc.

In the third step, the reaction product liquid from the second step is neutralized and acidified to convert the mercaptide into the vicinal dithiol. The reaction temperature of the third step largely influences the by-production of oligomers, etc. The by-production of oligomers, etc. can be prevented by carrying out the reaction at low temperatures, but the reaction time is prolonged. Therefore, it is not preferred for the production efficiency to unduly reduce the reaction temperature. To prevent the by-production of oligomers, etc. and to complete the reaction within a short period of time, the reaction temperature is preferably −20 to 40° C., more preferably −10 to 30° C., and still more preferably 0 to 20° C. Like the first step and the second step, the third step is performed preferably in an inert gas atmosphere.

The acid for use in the third step is not particularly limited as long as it neutralizes the bases used in the first step and the second step, and selected from known organic acids and inorganic acids. The acid may be added directly or after diluted. Examples of the acids are shown below.

(1) Organic Acids:

carboxylic acids such as formic acid, acetic acid, propionic acid, butyric acid, valeric acid, caproic acid, caprylic acid, naphthenic acid, methyl mercaptopropionate, oxalic acid, malonic acid, succinic acid, glutaric acid, adipic acid, maleic acid, cyclohexanecarboxylic acid, benzoic acid, phenylacetic acid, o-toluic acid, m-toluic acid, p-toluic acid, salicylic acid, 2-methoxybenzoic acid, 3-methoxybenzoic acid, benzoylbenzoic acid, phthalic acid, isophthalic acid, terephthalic acid, benzilic acid, α-naphthalenecarboxylic acid, β-naphthalenecarboxylic acid, thiodipropionic acid, dithiodipropionic acetic acid, peracetic acid, thioacetic acid, tartaric acid, maleic anhydride, benzoic anhydride, phthalic anhydride, trimellitic anhydride, and pyromellitic anhydride;

phosphoric mono and diesters such as mono- or dimethyl phosphate, mono- or diethyl phosphate, mono- or diisobutyl phosphate, mono- or dibutyl phosphate, and mono- or dilauryl phosphate;

phosphorous mono or diesters such as mono- or dimethyl phosphite, mono- or diethyl phosphite, mono- or diisobutyl phosphite, mono- or dibutyl phosphite, and mono- or dilauryl phosphite;

organic thiophosphorus compounds such as dialkyl phosphrodithioates including dimethyl phosphrodithioate;

phenols such as phenol, catechol, tert-butylcatechol, 2,6-di-tert-butylcresol, 2,6-di-tert-butylethylphenol, resorcinol, hydroquinone, phloroglucinol, pyrogallol, cresol, ethylphenol, butylphenol, nonylphenol, hydroxyphenylacetic acid, hydroxyphenylpropionic acid, hydroxyphenylacetic amide, methyl hydroxyphenylacetate, hydroxyphenethyl alcohol, hydroxyphenethylamine, hydroxybenzaldehyde, phenylphenol, bisphenol A, 2,2'-methylene-bis(4-methyl-6-tert-butylphenol), bisphenol F, bisphenol S, α-naphthol, β-naphthol, aminophenol, chlorophenol, and 2,4,6-trichlorophenol;

sulfonic acids such as methanesulfonic acid, ethanesulfonic acid, butanesulfonic acid, dodecanesulfonic acid, benzenesulfonic acid, o-toluenesulfonic acid, m-toluenesulfonic acid, p-toluenesulfonic acid, ethylbenzenesulfonic acid, butylbenzenesulfonic acid, dodecylbenzenesulfonic acid, p-phenolsulfonic acid, o-cresolsulfonic acid, metanilic acid, sulfanilic acid, 4B acid, diaminostilbenesulfonic acid, biphenylsulfonic acid, α-naphthalenesulfonic acid, β-naphthalene sulfonic acid, peri acid, Laurent acid, and phenyl-J acid; and sulfinic acids such as bennzenesulfinic acid and toluenesulfonic acid.

(2) Inorganic Acids:

nitric acid, hydrochloric acid, perchloric acid, hypochlorous acid, chlorine dioxide, hydrofluoric acid, sulfuric acid, fuming sulfuric acid, boric acid, arsenic acid, aresenous acid, pyroarsenic acid, phosphoric acid, phosphorous acid, hypophosphorous acid, phosphorus oxychloride, phosphorus oxybromide, phosphorus sulfide, phosphorus trichloride, phosphorus tribromide, phosphorus pentachloride, hydrocyanic acid, chromic acid, nitric anhydride, sulfuric anhydride, boron oxide, arsenic pentoxide, phosphorus pentoxide, chromic anhydride, sulfuryl chloride, silica gel, and silica-alumina.

The acid usable in the invention is not specifically limited to examples recited above, and the above acids may be used alone or in combination of two or more. Of the above acids, preferred are hydrochloric acid, sulfuric acid, nitric acid, boric acid and phosphoric acid. The acid may be added directly, but preferably added in the form of solution with an acid concentration of preferably 5% by weight to a saturated concentration, or a saturated concentration if the saturated concentration is less than 5% by weight. The acid is used in an amount so as to regulate the ratio of the total effective amount represented by the following formula:

$$\text{total effective amount} = V_a \times M_a \tag{2}$$

wherein $V_a$ is the valency of the acid and $M_a$ is the total molar number of the acid, to the total effective amount of the base used in the first step and the base added in the second step as defined by the formula 1 within the range of preferably 0.1 to 10, more preferably 0.5 to 5, and still more preferably 0.9 to 3.

In the third step, the acid or its solution is added dropwise to the reaction product liquid from the second step under stirring preferably over one minute to six hours, more preferably 10 min to 3 h, and still more preferably 30 min to 2 h to adjust the pH preferably to 1 to 7. After the dropwise addition, it is preferred to continue the stirring of the reaction liquid preferably for one minute to three hours, more preferably for 2 min to 2 h, and still more preferably for 5 minutes to one hour to allow the reaction to further proceed.

After the reaction, the resultant vicinal dithiol is separated from the reaction product liquid by known methods such as solvent extraction, washing, removal of solvent by distillation, etc. Examples of the extraction solvent include ether solvents, aromatic hydrocarbon solvents, aliphatic hydrocarbon solvents and halogenated hydrocarbon solvents. The extraction solvent may be added to the reaction product liquid prior to the addition of acid.

Examples of the extraction solvents are listed below.

(1) Ether Solvents:
ethyl ether, dichloroethyl ether, isopropyl ether, n-butyl ether, isoamyl ether, n-hexyl ether, methyl phenyl ether, ethyl phenyl ether, n-butyl phenyl ether, and amyl phenyl ether.

(2) Aromatic Hydrocarbon Solvents:
benzene, toluene and xylene.

(3) Aliphatic Hydrocarbon Solvents:
heptane, pentane, octane, nonane and decane.

(4) Halogenated Hydrocarbon Solvents:
methyl chloride, ethylene chloride, chloroform, carbon tetrachloride, ethyl chloride, 1,1,1-trichloroethane, and chlorobenzene.

The extraction solvent usable in the invention is not specifically limited to the examples recited above, and the above solvents may be used alone or in combination of two or more. Among the exemplified solvents, relatively preferred are aromatic hydrocarbon solvents, with toluene being more preferred.

The oxygen present in the reaction system from the first step through the third step is likely to cause the by-production of oligomers, etc. thereby to reduce the purity of the vicinal dithiol. Although the vicinal dithiol with an acceptable purity can be obtained even by the reaction in air, the reaction of each step is carried out in an atmosphere having an oxygen concentration of preferably 5% by volume or less, more preferably 3% by volume or less, and still more preferably 1% by volume or less.

The invention is described in more detail by reference to the following examples. However, it should be noted that the scope of the invention is not limited thereto.

The purity of the compound was measured by GPC under the following conditions:
column: Shodex GPC K-801,
temperature: 35° C.,
mobile phase: chloroform, and
detector: RID.

EXAMPLE 1

First Step

Into a flask equipped with a stirrer, a thermometer, a condenser, a dropping funnel and a nitrogen inlet, were charged 180 g of methanol, 0.290 g (6.74 mmol) of solid sodium hydroxide (content: 93%) and 61.5 g (808 mmol) of thioacetic acid. By blowing nitrogen gas into the flask, the contents were stirred to prepare a uniform solution and the oxygen concentration of the system was simultaneously reduced to 1% by volume or less. After raising the temperature of the solution to 50° C., 60.0 g (336 mmol) of bis(β-epithiopropyl) sulfide was added dropwise while maintaining the temperature at 50° C. After the dropwise addition, the reaction was allowed to further proceed at 50° C. for 4 h.

Second Step

After the reaction of the first step, the temperature of the solution was lowered to 10° C. Then, 84.1 g (841 mmol) of a 40% aqueous solution of sodium hydroxide was added dropwise while maintaining the temperature at 10° C. After the dropwise addition, the reaction was allowed to proceed at 10° C. for additional 9 h.

Third Step

After the reaction of the second step, 180 g of toluene was added. Then, the solution was neutralized and acidified by adding dropwise 270.5 g (890 mmol) of a 12% hydrochloric acid while maintaining the temperature at 10° C. The separated toluene layer was washed with 120 g of a 1% aqueous solution of sodium hydrogencarbonate and then washed twice with 120 g of water. By distilling off the toluene, 78 g of 1,2,6,7-tetramercapto-4-thiaheptane was obtained as a pale yellow liquid (94% crude yield and 94% purity).

$$H_2C-CH-CH_2-S-CH_2-CH-CH_2$$
$$\phantom{H_2C}|\phantom{-}|\phantom{-CH_2-S-CH_2-}|\phantom{-}|$$
$$\phantom{H_2C-}SH\ SH\phantom{-CH_2-S-CH_2-}SH\ SH$$

1,2,6,7-tetramercapto-4-thiaheptane

EXAMPLE 2

The reactions were carried out in the same manner as in Example 1 except for changing sodium hydroxide (6.74 mmol) used in the first step to sodium methoxide (6.74 mmol). The results are shown in Table 1.

EXAMPLE 3

The reactions were carried out in the same manner as in Example 1 except for changing the reaction temperatures of the second step and the third step from 10° C. to 30° C. The results are shown in Table 1.

EXAMPLE 4

The reactions were carried out in the same manner as in Example 1 except for omitting the blowing of nitrogen gas. The results are shown in Table

TABLE 1

| Examples | Oxygen concentration (%) | Base of first step | Reaction temperature of second and third steps (° C.) | Reaction time* of second step (h) | Crude yield (%) | Purity (%) |
| --- | --- | --- | --- | --- | --- | --- |
| 1 | <1 | NaOH | 10 | 9 | 94 | 94 |
| 2 | <1 | CH$_3$ONa | 10 | 9 | 94 | 94 |
| 3 | <1 | NaOH | 30 | 4 | 94 | 85 |
| 4 | 20 | NaOH | 10 | 9 | 93 | 80 |

*reaction time after completing the dropwise addition of base.

By the method of the invention including the reaction of an episulfide compound having at least one thiirane ring in its molecule and a thiocarboxylic S-acid, it has become possible to produce the vicinal dithiol in high yields. By carrying out the reactions of the second step and the third step at relatively low temperatures and by carrying out the overall process in low oxygen atmospheres, the production efficiency is effectively enhanced.

What is claimed is:

1. A method for producing a vicinal dithiol comprising a step of reacting an episulfide compound having at least one thiirane ring in its molecule with a thiocarboxylic S-acid.

2. The method according to claim 1, wherein the episulfide compound is represented by the following formula 1:

$$R^1-\overset{R^2\ R^3}{\underset{S}{\triangle}}-CH_2S[(CH_2)_mS]_nCH_2-\overset{R^4\ R^5}{\underset{S}{\triangle}}-R^6 \qquad (1)$$

wherein $R^1$ to $R^6$ are each independently hydrogen or $C_1$–$C_{10}$ hydrocarbon group, m is an integer from 0 to 6, and n is an integer from 0 to 4.

3. The method according to claim 1, wherein the thiocarboxylic S-acid is represented by the following formula 2:

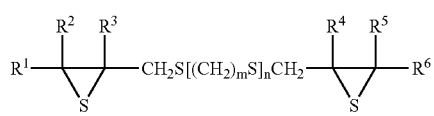

wherein $R^7$ is hydrocarbon group having 1 to 7 carbon atoms.

4. The method according to claim 1, comprising a first step of reacting the episulfide compound and the thiocarboxylic S-acid in the presence of a base to produce a thiocarboxylic S-ester; a second step of hydrolyzing the thiocarboxylic S-ester in the presence of a base to produce a mercaptide; and a third step of converting the mercaptide into the vicinal dithiol in the presence of an acid.

5. The method according to claim 4, wherein the bases for use in the first step and the second step are at least one compound selected from the group consisting of ammonia, amines, phosphines, metal alcoholates, metal hydrides, metal hydroxides, metal carbonates and metal sulfides.

6. The method according to claim 4, wherein the second step and the third step are conducted at −20 to 40° C.

7. The method according to claim 4, wherein each reaction of the first step through the third step is conducted in an atmosphere having an oxygen concentration of 5% by volume or less.

* * * * *